United States Patent
Schade et al.

(10) Patent No.: US 6,528,575 B1
(45) Date of Patent: *Mar. 4, 2003

(54) USE OF CROSSLINKED COPOLYMERS OF MONOETHYLENICALLY UNSATURATED CARBOXYLIC ACIDS AS STABILIZER IN OIL-IN-WATER EMULSIONS

(75) Inventors: Christian Schade, Ludwigshafen (DE); Horst Westenfelder, Neustadt (DE); Karin Sperling-Vietmeier, Neustadt (DE); Axel Sanner, Frankenthal (DE); Hans-Ulrich Wekel, Ellerstadt (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/578,706

(22) PCT Filed: Jul. 5, 1994

(86) PCT No.: PCT/EP94/02194

§ 371 (c)(1),
(2), (4) Date: Dec. 28, 1995

(87) PCT Pub. No.: WO95/03790

PCT Pub. Date: Feb. 9, 1995

(30) Foreign Application Priority Data

Jul. 28, 1993 (DE) .......................................... 43 25 158

(51) Int. Cl.⁷ .......................... A61K 7/48; A61K 9/113; C08K 3/20; C08F 20/04
(52) U.S. Cl. ...................... 524/559; 424/401; 524/556; 526/209; 526/213
(58) Field of Search ........................ 424/401; 526/209, 526/213; 524/556, 559

(56) References Cited

U.S. PATENT DOCUMENTS

| | | | | |
|---|---|---|---|---|
| 4,419,502 A | | 12/1983 | Sehm | 526/209 |
| 4,525,581 A | * | 6/1985 | Denzinger et al. | 528/503 |
| 4,871,536 A | * | 10/1989 | Arraudeau et al. | 424/63 |
| 4,927,627 A | * | 5/1990 | Schrader et al. | 424/62 |
| 5,017,365 A | * | 5/1991 | Niedbala | 424/59 |

FOREIGN PATENT DOCUMENTS

EP    268 164    5/1988

* cited by examiner

Primary Examiner—Robert E. L. Sellers
(74) Attorney, Agent, or Firm—Keil & Weinkauf

(57) ABSTRACT

The use of crosslinked copolymers obtainable by precipitation polymerization of monomer mixtures comprising (a) monoethylenically unsaturated $C_3$–$C_8$-carboxylic acids, their anhydrides or mixtures of said carboxylic acids and anhydrides, (b) compounds with at least 2 non-conjugated ethylenic double bonds in the molecule as crosslinkers and, where appropriate, (c) other monoethylenically unsaturated monomers which are copolymerizable with monomers (a) and (b), in the presence of free-radical polymerization initiators and from 0.1 to 20% by weight, based on the monomers used, of saturated, nonionic surface-active compounds, as stabilizer in oil-in-water emulsions in amounts of from 0.01 to 5% of the weight of the emulsions, and cosmetic and pharmaceutical formulations based on oil-in-water emulsions which contain said precipitation polymers.

5 Claims, No Drawings

USE OF CROSSLINKED COPOLYMERS OF MONOETHYLENICALLY UNSATURATED CARBOXYLIC ACIDS AS STABILIZER IN OIL-IN-WATER EMULSIONS

The present invention relates to the use of crosslinked copolymers which are prepared by precipitation polymerization of monomer mixtures comprising (a) monoethylenically unsaturated $C_3$–$C_8$-carboxylic acids, their anhydrides or mixtures of said carboxylic acids and anhydrides, (b) compounds with at least two non-conjugated ethylenic double bonds in the molecule as crosslinkers and, where appropriate, (c) other monoethylenically unsaturated monomers which are copolymerizable with monomers (a) and (b), in the presence of free-radical polymerization initiators and certain surface-active compounds, and to cosmetic or pharmaceutical formulations based on oil-in-water emulsions containing the abovementioned crosslinked copolymers as stabilizer.

DE-B-1 138 225 discloses a process for preparing water-insoluble, water-swellable copolymers by precipitation polymerization of monoethylenically unsaturated carboxylic acids, monomers with at least two non-conjugated ethylenic double bonds in the molecule as crosslinkers and, where appropriate, other water-insoluble monoethylenically unsaturated monomers in the presence of free-radical polymerization initiators and of protective colloids and/or emulsifiers which are soluble both in organic solvents and in water. Thus, for example, precipitation polymerization of acrylic acid and butanediol diacrylate in 1,2-dichloroethane in the presence of polyvinyl ether results in a fine powder which, in ammonia-containing water, forms stiff gels which are suitable as ointment bases for cosmetics. The crosslinked polymers are used in particular as swelling or thickening agents.

DE-A-2 949 843 discloses a process for preparing crosslinked polymers of monoethylenically unsaturated carboxylic acids by free-radical precipitation polymerization of the monomers in the presence of free-radical polymerization initiators and homopolymers of vinylpyrrolidone as protective colloid. The precipitation polymers are used as thickeners in the drugs, cosmetics, paper, textiles, adhesives and emulsion paint sectors.

In the process discosed in DE-A-2 833 468, for example, copolymers of acrylic acid or methacrylic acid and acrylic esters or methacrylic esters are subjected to precipitation polymerization in the presence of ethylene/propylene rubber where appropriate in the presence of crosslinkers. The fine-particle polymers obtainable in this way are used as thickeners in printing pastes, paper coatings and aqueous paint emulsions.

U.S. Pat. No. 4,419,502 discloses the polymerization of monoethylenically unsaturated carboxylic acids in the presence of crosslinkers, free-radical polymerization initiators and polyoxyethylene alkyl ethers and/or polyoxyethylene sorbitan esters in methylene chloride. The surfactants which are also used in the precipitation polymerization serve to control the particle size of the polymers, improve the stirrability of the polymerization mixture and prevent deposits forming in the reaction vessel.

EP-A-0 268 164 discloses storage-stable, rapidly breaking oil-in-water emulsions which comprise a copolymer of acrylic acid with a minor content of a long-chain alkyl acrylate as stabilizer. As stated on page 8 of this citation, permanent stabilization of oil-in-water emulsions is not possible by adding homopolymers of acrylic acid or slightly crosslinked polyacrylic acids.

The earlier non-prior-published DE Application P 4213283.5 discloses the use of copolymers of monoethylenically unsaturated carboxylic acids and long-chain compounds with isolated CC multiple bonds and, where appropriate, further copolymerizable monomers and crosslinkers as thickeners or dispersants, for example in cosmetic or pharmaceutical formulations. The copolymers are prepared by precipitation polymerization.

It is an object of the present invention to provide other stabilizers for oil-in-water emulsions.

We have found that this object is achieved by using crosslinked polymers obtainable by precipitation polymerization of monomer mixtures comprising (a) monoethylenically unsaturated $C_3$–$C_8$-carboxylic acids, their anhydrides or mixtures of said carboxylic acids and anhydrides, (b) compounds with at least two non-conjugated ethylenic double bonds in the molecule as crosslinkers and, where appropriate, (c) other monoethylenically unsaturated monomers which are copolymerizable with monomers (a) and (b), in the presence of free-radical polymerization initiators and from 0.1 to 20% by weight, based on the monomers used, of saturated, nonionic surface-active compounds, as stabilizer in oil-in-water emulsions in amounts of from 0.01 to 5% of the weight of the emulsions.

The present invention also relates to cosmetic or pharmaceutical formulations based on oil-in-water emulsions which contain as stabilizer from 0.01 to 5% by weight of crosslinked polymers obtainable by precipitation polymerization of monomers mixtures comprising (a) monoethylenically unsaturated $C_3$–$C_8$-carboxylic acids, their anhydrides or mixtures of said carboxylic acids and anhydrides, (b) compounds with at least two non-conjugated ethylenic double bonds in the molecule as crosslinkers and, where appropriate, (c) other monoethylenically unsaturated monomers which are copolymerizable with monomers (a) and (b), in the presence of free-radical polymerization initiators and from 0.1 to 20% by weight, based on the monomers used, of saturated, nonionic surface-active compounds.

Suitable crosslinked copolymers are prepared by precipitation polymerization of monomer mixtures. Component (a) used in the monomer mixtures comprises monoethylenically unsaturated $C_3$–$C_8$-carboxylic acids, their anhydrides or mixtures of said carboxylic acids and anhydrides. Examples of suitable carboxylic acids are acrylic acid, methacrylic acid, maleic acid, fumaric acid, itaconic acid, crotonic acid and 2-pentenoic acid. Examples of suitable anhydrides are methacrylic anhydride, maleic anhydride and itaconic anhydride. Monomers of group (a) which are preferably used are acrylic acid, methacrylic acid, maleic acid, maleic anhydride and/or methacrylic anhydride. Monomers (a) can be present, for example, in the mixtures used for the polymerization in amounts of from 50 to 99,99, preferably from 80 to 99,99, % by weight.

Suitable as monomer of group (b) are compounds with at least two non-conjugated ethylenic double bonds in the molecule. Monomers of this type are normally used as crosslinkers in polymerizations. They increase the molecular weight of the resulting copolymers. Examples of suitable crosslinkers are the diacrylates or dimethacrylates of glycols or polyalkylene glycols, such as ethylene glycol diacrylate, ethylene glycol dimethacrylate, diethylene glycol methacrylate, diethylene glycol diacrylate or diacrylates or dimethacrylates of polyethylene glycols with molecular weights of up to 2000, divinylbenzene, divinyldioxane, divinylethyleneurea, diallyltartaramide, methylenebisacrylamide, polyhydric alcohols which are esterified at least twice with acrylic acid or methacrylic acid, such as trimethylolpropane, pentaerythritol, 1,4-butanediol, 1,6-hexanediol and sorbitol, trivinylcyclohexane, triallyltriazinetrione, allyl esters of acrylic acid and methacrylic acid, and allyl ethers of polyhydric alcohols, eg. the di- and triallyl ethers of trimethylolpropane, pentaerythritol, sorbitol and sucrose. Crosslinkers which are preferably used are pentaerythritol triallyl ethers, diacrylates or dimethacrylates of glycols or polyethylene glycols with molecular weights of up to 2000, pentaallylsucrose, allyl methacrylate, trimethylolpropane diallyl ether and/or methylenebisacrylamide. The amounts of crosslinker in the monomer mixture are preferably from 0.01 to 20% by weight. In most cases, the monomer mixtures used for the polymerization contain from 0.1 to 2% by weight of crosslinker, it also being possible to use mixtures of different crosslinkers.

Examples are further monoethylenically unsaturated monomers of group (c) suitable for copolymerization with monomers (a) and (b) of N-vinylpyrrolidone, N-vinylcaprolactam, $C_1$–$C_{18}$-alkyl (meth)acrylates, for example methyl acrylate, methyl methacrylate, ethyl acrylate, ethyl methacrylate, propyl acrylate, propyl methacrylate, n-butyl acrylate, n-butyl methacrylate, isobutyl acrylate, isobutyl methacrylate, 2-ethylhexyl acrylate, 2-ethylhexyl methacrylate, stearyl acrylate or stearyl methacrylate, acrylamide, methacrylamide, N-($C_1$–$C_8$-alkyl)acrylamides or -methacrylamides such as N,N-dimethylacrylamide, N,N-dimethylmethacrylamide, N-tert-butylacrylamide, N-tert-butylmethacrylamide, N-tert-octylacrylamide or N-tert-octylmethacrylamide, vinyl esters of saturated $C_1$–$C_8$-carboxylic acids, such as vinyl acetate, vinyl propionate, vinyl butyrate or vinyl stearate, styrene, phenoxyethyl acrylate, hydroxyalkylene monoacrylic esters and hydroxyalkylene monomethacrylic esters with, in each case, 2 to 6 carbon atoms in the alkylene chain or acrylic esters and methacrylic esters of ethoxylated $C_1$–$C_{18}$-alcohols, where from 2 to 25 ethylene oxide units have been added per mol of alcohol. If the compounds of the group (c) are used to modify the copolymers, their content in the monomer mixture is up to 49.89, preferably from 0 to 19.09, % by weight. Monomers of group (c) which are preferably used are N-vinylpyrrolidone, $C_1$–$C_{18}$-alkyl (meth)acrylates, styrene, hydroxyethyl (meth)acrylate and ethyl diglycol acrylate.

The crosslinked copolymers to be used according to the invention are prepared in the presence of specific surface-active compounds. One group of these surface-active compounds comprises saturated, nonionic surfactants such as esters of sugars or sugar derivatives, such as sucrose esters, mannose esters, xylose esters or sorbitan esters, esters and ethers of glycerol, polyglycerol or glycerol/sugar condensates, ceramides and glycosyl-ceramides, fatty acid alkanolamides such as fatty acid ethanolamides, fatty acid isopropanolamides, fatty acid diethanolamides, fatty acid polydiethanolamides, N-alkylpyrrolidone derivatives, alkyl pyrrolidone-5-carboxylates, citric and tartaric esters, $C_1$–$C_{18}$-alkyl (poly)glycosides, hydroxyalkyl polyglycosides, fatty acid esters of polyhydroxy compounds such as trimethylolpropane, erythritol, pentaerythritol, neopentyl diglycol, triethanolamine or condensates derived therefrom, alkoxylates, in particular the adducts of ethylene oxide and/or propylene oxide with the compounds listed above, and with oxo alcohols, $C_8$–$C_{30}$-alcohols, alkylphenols, fatty acid amides, fatty amines, fatty acids and derivatives such as hydroxy carboxylic acids, it being possible for the polyalkylene oxide chains to be modified at one end or both ends. In the caes of modification at both ends, the modifying components can be identical or different and, for example, in part also represent a $C_1$–$C_4$-ether functionality.

Polymeric surfactants which contain ethylene oxide and/or propylene oxide units as hydrophilic part of the molecule are uncrosslinked and have molecular weights of from 500 to 100,000, preferably 700 to 20,000. The polymeric surfactants may, besides at least one hydrophilic block, contain at least one hydrophobic block or are composed of a hydrophilic chain with hydrophobic branches arranged in the manner of a comb. The hydrophilic part of the polymeric surfactants is formed by homopolymers of ethylene oxide or propylene oxide or of block copolymers of ethylene oxide and propylene oxide and of block and comb polymers with blocks of polyethylene oxide, polypropylene oxide or polyco(ethylene oxide, propylene oxide), whereas the hydrophobic part of the polymeric surfactants comprises blocks of polystyrenes, polyalkyl (meth)acrylates, silicone oils, polyhydroxy fatty acids, polyamidoamines, polyisobutyls or polytetrahydrofurans. It is also possible for general polymers which have at least one amino group, a hydroxyl group which can be deprotonated with bases, or an anionic group and have a molecular weight of from 100 to 5000 to be reacted with ethylene oxide, propylene oxide or mixtures thereof to give suitable polymeric surfactants.

Further surface-active compounds are sorbitan esters, sucrose esters or glycerol esters of saturated $C_8$–$C_{30}$-carboxylic acids or alkoxylation products of these esters. The abovementioned esters are preferably derived from $C_{12}$–$C_{22}$-carboxylic acids. Alkoxylation products are preferably the adducts of ethylene oxide with the esters. Up to 80 mol of ethylene oxide can be added per mol of the suitable esters. Also suitable as surface-active compounds are adducts of ethylene oxide and propylene oxide and/or butylene oxides with the esters.

Further saturated, nonionic surface-active compounds are hydrophobically modified cellulose and/or starch, such as ethylcelluloses, hydroxypropylmethylcelluloses, methylcelluloses, hydroxypropylcelluloses or cellulose triacetate.

The saturated, nonionic surface-active compounds of those mentioned above which are preferably used are sucrose esters, sorbitan esters, glycerol esters, alkyl (poly) glycosides, adducts of ethylene oxide with the abovementioned compounds and adducts of ethylene oxide with $C_{12}$–$C_{22}$-alcohols, and the use of sorbitan stearate, sorbitan monolaurate and hydrogenated castor oil ethoxylates is particularly preferred.

The above-described surfactants, as well as the polymeric surfactants and modified celluloses and starches, are surface-active compounds. They consist of a hydrophobic part and a hydrophilic part. When they have sufficient solubility in water, they have a surface tension measured in 1% by weight aqueous solution against air of less than 66 mN/m at 20° C.

The above-described surface-active compounds are used in the precipitation polymerization in amounts of from 0.1 to 20, preferably 0.25 to 10, % of the weight of the monomers.

The precipitation polymerization is normally carried out in a solvent in which the monomers are soluble and the resulting polymers are insoluble. Examples of suitable solvents are aromatic and saturated aliphatic hydrocarbons. Examples of aromatic hydrocarbons are benzene, toluene, xylene and isopropylbenzene. The saturated aliphatic hydrocarbons preferably have from 5 to 12 carbon atoms. Pentane, pentane, n-hexane, cyclohexane, octane and isooctane are suitable. The precipitation polymerization can also be carried out in halogenated saturated aliphatic hydrocarbons such as 1,1,1-trichloroethane or methylene chloride. Also suitable as reaction medium are ethers, $C_2$–$C_6$-alkyl esters of formic acid or acetic acid, ketones with from 3 to 6 carbon atoms, liquid or supercritical carbon dioxide. Examples of suitable ethers are tert-butyl methyl ether and isobutyl methyl ether. The alkyl esters of formic acid or acetic acid are preferably derived from saturated alcohols with from 2 to 6 carbon atoms, eg. ethyl formate, methyl acetate or ethyl acetate. Examples of suitable ketones are acetone and methyl ethyl ketone. The diluents can be used alone or mixed with one another. The diluents preferably used in the precipitation polymerization are saturated aliphatic hydrocarbons with from 5 to 8 carbon atoms in the molecule, which can be straight-chain or branched, cyclic or bicyclic. Cyclohexane is particularly preferably used as solvent in the precipitation polymerization. The amount of solvent is chosen so that the reaction mixture can be stirred during the polymerization. The solids content of the mixture after the polymerization is preferably in the range from 10 to 40% by weight.

The molecular weight of the copolymers can, if required, be reduced by adding regulators to the polymerizing mixture. Examples of suitable regulators are mercapto compounds such as dodecyl mercaptan, thioethanol, thioglycolic acid or mercaptopropionic acid. If regulators are used, they are employed in amounts of from 0.1 to 5% of the weight of the monomers.

The copolymerization takes place in the presence of free-radical polymerization initiators. Suitable compounds of this type are azo or peroxo compounds, eg. diacyl peroxides such as dilauroyl peroxide, didecanoyl peroxide and dioctanoyl peroxide, or peresters such as tert-butyl peroctanoate, tert-butyl perpivalate, tert-amyl perpivalate or tert-butyl perneodecanoate, and azo compounds such as dimethyl 2,2'-azobis(isobutyrate), 2,2'-azobis (isobutyronitrile), 2,2'-azobis(2-methylbutyronitrile) or 2,2'-azobis(2,4-dimethylvaleronitrile). The initiators are used in the amounts customary in precipitation polymerization, eg. in amounts of from 0.05 to 5% of the weight of the monomers. If water and/or bases are also used in the precipitation polymerization, the amounts are only such that the mixture of all the components just appears homogeneous before the polymerization starts.

The precipitation polymerization is normally carried out under an inert gas atmosphere. The copolymerization can be carried out, for example, in such a way that all the components present during the polymerization are introduced into a polymerization vessel and the reaction is started, and the reaction mixture is cooled where appropriate to control the temperature. However, it is also possible to proceed in such a way that only some of the components to be polymerized are introduced, the polymerization is started, and the remainder of the mixture to be polymerized is metered in continuously or batchwise depending on the progress of the polymerization. However, it is also possible to proceed in such a way that the diluent is initially introduced together with a surfactant, and the monomers and the polymerization initiator are separately added thereto continuously or batchwise.

The temperature during the polymerization is generally from 40 to 160, preferably 50 to 120, °C. It can be controlled in various ways during the reaction by a program. The polymerization is preferably carried out under atmospheric pressure but can also be carried out under reduced or elevated pressure. If the polymerization temperature is above the boiling point of the inert diluent, the polymerization is carried out in pressure-tight apparatus under pressures of up to 8 bar. If carbon dioxide is used as inert diluent, the polymerization is normally carried out in an autoclave above the critical temperature of carbon dioxide. The pressures are then above 73 bar.

The polymerization process is preferably controlled in such a way that the copolymer results in the form of a fine-particle powder. The average particle size of the polymer powder is from 0.1 to 500, preferably 0.5 to 200, $\mu$m. After the polymerization, the crosslinked copolymer is separated from the other components of the reaction mixture, for example by filtration, decantation or centrifugation. The resulting powder can, where appropriate, be subjected to further suitable separation, washing, drying or milling processes.

Particularly interesting precipitation polymers are those obtainable by copolymerization of monomer mixtures comprising a) 80–99,99% by weight of acrylic acid, methacrylic acid, maleic acid, maleic anhydride and/or methacrylic anhydride and b) 0.01–20% by weight of pentaerythritol triallyl ether, diacrylates or dimethacrylates of glycols or polyethylene glycols with molecular weights of up to 2000, pentaallylsucrose, allyl methacrylate, trimethylolpropane diallyl ether and/or methylenebisacrylamide.

The resulting copolymers are crosslinked and insoluble in water, but they swell in water.

The above-described copolymers are used as stabilizer in oil-in-water emulsions in amounts of from 0.01 to 5% of the weight of the emulsions. They are suitable for stabilizing all oil-in-water emulsions, eg. water-in-oil polymer emulsions, antifoam agents based on oil-in-water emulsions, textile printing pastes, paints, cleaner formulations, oil well muds, liquid detergents and, in particular, for stabilizing cosmetic or pharmaceutical formulations based on oil-in-water emulsions.

In order to achieve permanent stabilization of oil-in-water emulsions, the dispersed polymer is neutralized sufficiently with a base. Examples of suitable bases are alkali metal bases such as alkali metal hydroxides and carbonates, for example NaOH, KOH and sodium and potassium carbonate, ammonia and organic amines, pyridines and amidines or mixtures thereof. On neutralization with organic amines, those preferably used are alkanolamines from the series of mono-, di- or trialkanolamines with from 2 to 5 carbon atoms in the alkanol residue such as mono-, di- or triethanolamine, mono-, di- or tri(iso)propanolamine or 2-amino-2-methylpropanol, alkanediolamines with from 2 to 4 carbon atoms in the alkanediol residue such as 2-amino-2-methyl-1,3-propanediol or 2-amino-2-ethyl-1,3-propanediol, alkanepolyolamines such as tris (hydroxymethyl)aminomethane or N,N,N',N'-tetrakis(2-hydroxypropyl)ethylenediamine, alkylamines such as di(2-ethylhexyl)amine, triamylamine or dodecylamine and amino ethers such as morpholine.

The cosmetic or pharmaceutical formulations may moreover contain as oil any of the oils customarily used for this purpose. The total amount of the oil phase in the emulsion can be up to 80% by weight. The amount of the oil phase in the cosmetic or pharmaceutical formulations is preferably from 10 to 50% by weight. The slightly crosslinked copolymers are preferably used to stabilize creams or lotions. They are also very suitable for thickening aqueous systems or forming thickened gels after the dispersed copolymer has been utilized sufficiently by adding a base, eg. triethanolamine, sodium hydroxide solution, potassium hydroxide solution, 2-amino-2-methyl-1-propanol, 2-amino-2-methyl-1,3-propanediol, diisopropanolamine or tetrahydroxypropylethylenediamine.

In contrast to slightly crosslinked homopolymers of acrylic acid, it is possible with the slightly crosslinked copolymers to be used according to the invention to stabilize oil-in-water emulsions permanently. The amount of crosslinked copolymers preferably used is from 0.05 to 2% of the weight of the emulsions.

EXAMPLES

Determination of Gel Viscosity 1 g of a crosslinked copolymer and 200 g of water are weighed into a 300 ml beaker and stirred until homogeneous. Then 1 ml of triethanolamine is added, and the mixture is stirred until a homogeneous mixture is produced. A Haake VT-02 manual viscometer with spindle 1 is then used to determine the viscosity of the mixture at 20° C. and 60 rpm.

Polymer 1

1320 ml of cyclohexane, 50 g of acrylic acid, 1.5 g of pentaerythritol triallyl ether, 7.5 g of sorbitan stearate and 80 mg of 2,2'-azobis(2-methylbutyronitrile) were introduced into a 3000 ml flask equipped with a stirrer and an apparatus for working under protective gas, and the mixture was heated to 80° C. while stirring under a stream of nitrogen. After this temperature was reached, 200 g of acrylic acid were added dropwise over the course of 2 hours and, separately, 80 ml of cyclohexane and 320 mg of 2,2'-azobis (2-methylbutyronitrile) were added dropwise over the course of 3 hours. After the addition of the polymerization initiator was complete, the mixture was stirred at 80° C. for 3 hours. The product was then filtered off on a suction funnel and dried in a vacuum oven at 50° C. for 8 hours. 251 g of a white polymer powder with a gel viscosity of 7 Pa·s were obtained.

Polymer 2

1320 ml of cyclohexane, 50 g of acrylic acid, 1.2 g of pentaerythritol triallyl ether, 1.5 g of triglyceryl distearate and 80 mg of 2,2'-azobis(2-methylbutyronitrile) were introduced into a 3000 ml flask equipped with a stirrer and an apparatus for working under protective gas, and the mixture was heated to 80° C. while stirring under a stream of nitrogen. After this temperature was reached, 200 g of acrylic acid and 6 g of triglyceryl distearate were added dropwise over the-course of 2 hours and, separately, 80 ml of cyclohexane and 320 mg of 2,2'-azobis(2-methylbutyronitrile) were added dropwise over the course of 3 hours. After the addition of the polymerization initiator was complete, the mixture was stirred at 80° C. for 3 hours. The product was then filtered off on a suction funnel and dried in a vacuum oven at 50° C. for 8 hours. 251 g of a white polymer powder with a gel viscosity of 7.5 Pa·s were obtained.

Polymer 3

1320 ml of cyclohexane, 50 g of acrylic acid, 1.5 g of pentaerythritol triallyl ether, 80 mg of 2,2'-azobis(2-methylbutyronitrile) and 7.5 g of a hydrogenated castor oil ethoxylate with 47 ethylene oxide units in the molecule were introduced into a 3000 ml flask equipped with a stirrer and an apparatus for working under protective gas, and the mixture was heated to 80° C. while stirring under a stream of nitrogen. After this temperature was reached, 200 g of acrylic acid were added dropwise over the course of 2 hours and, separately, 80 ml of cyclohexane and 320 mg of 2,2'-azobis(2-methylbutyronitrile) were added dropwise over the course of 3 hours. After the addition of the polymerization initiator was complete, the mixture was stirred at 80° C. for 3 hours. The product was then filtered off on a suction funnel and dried in a vacuum oven at 50° C. for 8 hours. 234 g of a white polymer powder with a gel viscosity of 11 Pa·s were obtained.

Polymer 4

A polymer was prepared from 250 g of acrylic acid, 1.5 g of pentaerythritol triallyl ether and 7.5 g of sucrose stearate as for the preparation of polymer 3. 255 g of a white polymer powder with a gel viscosity of 7 Pa·s were obtained.

Polymer 5

A polymer was prepared from 250 g of acrylic acid, 1.2 g of pentaerythritol triallyl ether and 7.5 g of a cellulose ether with a degree of substitution of 46% and a viscosity of 0.1 Pa·s [measured in a 5% strength solution in toluene/ethanol=4:1 (v/v) at 25° C., Ubbelohde viscometer] as for the preparation of polymer 3. 243 g of a white polymer powder with a gel viscosity of 10.5 Pa·s were obtained.

Polymer 6

A polymer was prepared from 250 g of acrylic acid, 1.5 g of pentaerythritol triallyl ether and 7.5 g of cetearyl polyglycoside as for the preparation of polymer 3. 250 g of a white polymer powder with a gel viscosity of 8.5 Pa·s were obtained.

Polymer 7

A polymer was prepared from 250 g of acrylic acid, 1.5 g of allyl methacrylate and 7.5 g of an ethylene oxide/propylene oxide block copolymer with a molecular weight of 2000 and a cloud point in water of 23° C. as for the preparation of polymer 3. 247 g of a white polymer powder with a gel viscosity of 7 Pa·s were obtained.

Polymer 8

A polymer was prepared from 250 g of acrylic acid, 1.5 g of pentaerythritol triallyl ether and 7.5 g of a polystyrene/polyethylene oxide block copolymer with a molecular weight of 2000 and a styrene/ethylene oxide ratio of 1:1 as for the preparation of polymer 3. 253 g of a white polymer powder with a gel viscosity of 10 Pa·s were obtained.

Polymer 9

A polymer was prepared from 250 g of acrylic acid, 1.2 g of pentaerythritol triallyl ether and 7.5 g of sorbitan monolaurate as for the preparation of polymer 3. 248 g of a white polymer powder with a gel viscosity of 8 Pa·s were obtained.

Polymer 10

A polymer was prepared from 250 g of acrylic acid, 1.2 g of pentaerythritol triallyl ether and 12.5 g of a myristyl alcohol which had been reacted with 2.5 ethylene oxide and 5 propylene oxide units per molecule as for the preparation of polymer 3. 258 g of a white polymer powder with a gel viscosity of 9 Pa·s were obtained.

Polymer 11

A polymer was prepared from 250 g of acrylic acid, 1.2 g of pentaerythritol triallyl ether and 7.5 g of coconut fatty acid diethanolamide as for the preparation of polymer 3. 234 g of a white polymer powder with a gel viscosity of 5 Pa·s were obtained.

Polymer 12

A polymer was prepared from 250 g of acrylic acid, 1.5 g of pentaerythritol triallyl ether and 7.5 g of a polyoxyethylene sorbitan monolaurate with a degree of ethoxylation of 20 as for the preparation of polymer 3. 252 g of a white polymer powder with a gel viscosity of 8 Pa·s were obtained.

Comparative Example 1

1320 ml of cyclohexane, 50 g of acrylic acid, 0.3 g of pentaerythritol triallyl ether and 80 mg of 2,2'-azobis(2-methylbutyronitrile) were introduced into a 3000 ml flask equipped with a stirrer and an apparatus for working under protective gas, and the mixture was heated to 80° C. while stirring under a stream of nitrogen. After this temperature was reached, 200 g of acrylic acid and 1.2 g of pentaerythritol triallyl ether were added dropwise over the course of 2 hours and, separately, 80 ml of cyclohexane and 320 mg of 2,2'-azobis(2-methylbutyronitrile) were added dropwise over the course of 3 hours. After the addition of the polymerization initiator was complete, the mixture was stirred at 80° C. for 3 hours. The product was then filtered off on a suction funnel and dried in a vacuum oven at 50° C. for 8 hours. 247 g of a white polymer powder with a gel viscosity of 13 Pa·s were obtained.

Preparation and Assessment of Liquid Paraffin/Water Emulsions 0.4 g of polymer and 30 g of liquid paraffin are weighed into a 300 ml vessel and stirred until homogeneous. Then 103.6 ml of water are added and the mixture is stirred for 30 min. Finally, 0.4 g of triethanolamine is added and the mixture is stirred to give a preemulsified phase. Subsequently, the mixture is treated in a disperser until a homogeneous white emulsion with an average particle size of the emulsified oil phase of less than 50 μm is produced. The emulsion is transferred into a 100 ml measuring cylinder which is stoppered and stored at 25° C. for one week. Emulsions 1–5 (Comparison with Prior Art)

Emulsions were prepared with the polymer from Comparative Example 1 and the amount indicated below of a surfactant according to the stated method.

Emulsion 1: 12 mg of sorbitan stearate

Emulsion 2: 12 mg of hydrogenated castor oil ethoxylate with 47 ethylene oxide units in the molecule Emulsion 3: 12 mg of cetearyl polyglycoside Emulsion 4: 12 mg of sorbitan monolaurate Emulsion 5: 50 mg of sorbitan monolaurate All the emulsions began to separate after 12–24 hours at the most and showed two separate phases after 60 h at the most.

Examples 1–11

Emulsions were prepared with polymers 1–11 by the method indicated above. All the emulsions were still stable after 170 hours and showed no tendency to separate.

Examples 12–18

Oil-in-water emulsions were prepared with polymer 3 by the stated method, using the following oils in place of liquid paraffin:

Example 12: Arachis oil

Example 13: Jojoba oil

Example 14: Capric acid triglyceride

Example 15: linear polydimethylsiloxane, viscosity 0.35 Pa·s

Example 16: Isostearic acid

Example 17: Decyl oleate

Example 18

Ethylhexanoic Ester of a $C_{16}/C_{18}$ Fatty Alcohol

All the emulsions were still stable after 170 hours and showed no tendency to separate.

Examples 19–22

Liquid paraffin/water emulsions were prepared by the method indicated above using polymer 8 and replacing the amount of oil used by the stated amount:

Example 19: 15 g of liquid paraffin

Example 20: 45 g of liquid paraffin

An emulsion was prepared with polymer 8 by the stated method, replacing the amount of polymer used by the stated amount:

Example 21: 0.27 g

Example 22: 0.53 g

All the emulsions were still stable after 170 hours and showed no tendency to separate.

We claim:

1. A process for stabilizing an oil-in-water emulsion which process comprises adding to the emulsion from 0.01 to 5% by weight of the emulsion of a crosslinked copolymer obtained by precipitation polymerization of a monomer mixture comprising:

(a) monoethylenically unsaturated $C_3$–$C_8$-carboxylic acids, their anhydrides or mixtures of the carboxylic acids and anhydrides, (b) compounds with at least 2 non-conjugated ethylenic double bonds in the molecule as crosslinkers and, optionally, (c) other monoethylenically unsaturated monomers which are copolymerizable with monomers (a) and (b), in the presence of free-radical polymerization initiators and from 0.1 to 20% by weight, based on the total weight of the monomers of a saturated, nonionic surface-active compound.

2. The process of claim 1, wherein the saturated, nonionic surface-active compound is a member selected from the group consisting of sorbitan esters or sucrose esters or glycerol esters of saturated $C_8$–$C_{30}$-carboxylic acids, and alkoxylation products of these esters.

3. The process of claim 1, wherein the saturated, nonionic surface-active compound is a member selected from the group consisting of hydrophobically modified cellulose and hydrophobically modified starch.

4. The process of claim 1, wherein the monomer mixture comprises:

a) 80–99.99% by weight of a member selected from the group consisting of acrylic acid, methacrylic acid, maleic acid, maleic anhydride, and methacrylic anhydride, and b) 0.01–20% by weight of a member selected from the group consisting of pentaerythritol triallyl ether, diacrylates or dimethacrylates of glycols or polyethylene glycols with molecular weights up to 2000, pentaallylsucrose, allyl methacrylate, trimethylolpropane diallyl ether, and methylenedisacrylamide.

5. The process of claim 1, wherein the oil-in-water emulsion is a cosmetic or pharmaceutical oil-in-water emulsion.

* * * * *